(12) United States Patent
Hultine et al.

(10) Patent No.: US 6,268,399 B1
(45) Date of Patent: Jul. 31, 2001

(54) SALAL EXTRACTS HAVING ANTIMICROBIAL PROPERTIES

(75) Inventors: J. Dustin Hultine, Portland; Takuji Tsukamoto, Bend, both of OR (US)

(73) Assignee: Menlo West, LLC, Portland, OR (US)

( * ) Notice: Subject to any disclaimer, the term of this patent is extended or adjusted under 35 U.S.C. 154(b) by 0 days.

(21) Appl. No.: 09/527,966

(22) Filed: Mar. 17, 2000

(51) Int. Cl.⁷ ..................................... A61K 47/00
(52) U.S. Cl. ............................................. 514/784
(58) Field of Search ............................... 514/784

(56) References Cited

U.S. PATENT DOCUMENTS 4,523,589 * 6/1985 Krauser ........................... 128/203.27

* cited by examiner

Primary Examiner—Zohreh Fay
(74) Attorney, Agent, or Firm—Chernoff, Vilhauer McClung & Stenzel, LLP

(57) ABSTRACT

Extracts of the common edible evergreen plant *Gaultheria shallon,* commonly known as salal, are shown to have bactericidal and fungicidal activity.

21 Claims, No Drawings

SALAL EXTRACTS HAVING ANTIMICROBIAL PROPERTIES

BACKGROUND OF THE INVENTION

While a wide variety of Staphylococcus bacteria are known to exist, one particularly troublesome bacteria to man and animals is *Staphylococcus aureus*, an extremely common skin bacteria commonly referred to simply as "staph."

Occasionally, staph can get into the body and cause an infection. This infection can be minor (such as pimples, boils, and other skin conditions) or serious (such as blood infections or pneumonia). When *S. aureus*, which often lives harmlessly on mucous membranes, gains access to the bloodstream or deep tissue through a wound, incision or medical device, it can rapidly damage the heart, lungs, brain or joints, or poison the entire system. Surveys conducted by the U.S. Centers for Disease Control indicate that such more serious infections occur in one out of 1,400 hospital patients-a third of whom die as a result of the infection.

Methicillin is an antibiotic commonly used to treat staph infections. Although methicillin is very effective in treating most staph infections, a substantial percentage, on the order of 40%, staph bacteria have developed resistance to methicillin and can no longer be killed by this antibiotic. These resistant bacteria are called methicillin-resistant *Staphylococcus aureus*, or MRSA. The antimicrobial agent vancomycin has been used to treat many *S. aureus* infections, particularly those caused by MRSA. However, *S. aureus* now appears to be developing resistance even to vancomycin, as documented by recent cases in the U.S., France, Japan and China. There is therefore a need in the art for a non-toxic agent exhibiting bactericidal properties against common Staphylococcus bacteria and in particular against *S. aureus*.

The fungus Verticillium is a common mold found in agricultural settings that attacks more than 200 woody and herbaceous plant species, causing so-called "Verticillium wilt," which ultimately kills the plant. Although five different chemical soil fumigants are known for treating Verticillium wilt, three of the five (trichloronitromethane, methyl bromide and Vorlex) are toxic to humans and animals, and two (sodium methyldithiocarbamate and 1,3 dichloropropene) are classified by the Environmental Protection Agency as potential human carcinogens. There is therefore a need in the art for a non-toxic agent exhibiting antifungal activity, in particular against Verticillium.

BRIEF SUMMARY OF THE INVENTION

There are several aspects of the present invention. In its broadest aspect, the invention comprises an antimicrobial composition comprising an extract of the salal plant. In a closely related aspect the invention comprises a bactericidal composition comprising an extract of the salal plant. In another closely related aspect the invention comprises a fungicidal composition comprising the same extract. Still another aspect of the invention comprises a method of extracting such antimicrobial agents from the salal plant.

DETAILED DESCRIPTION OF THE INVENTION

*Gaultheria shallon*, commonly known as salal, is of the Ericaceae or heather family, being an evergreen shrub typically indigenous to the Pacific Coast and in particular to the northern coast of California and the coasts of Oregon and Washington. The leaves are leathery and sharply and finely toothed. The flowers are urn-shaped, white to pink, and falling in clusters at branch ends, generally oriented in one direction. Flowering occurs from mid-May to the beginning of July, followed by the bearing of fruit consisting of berries that are usually mature by mid-August and which continue into late summer and early fall.

All parts of the plant, including its dark juicy berries, are edible and are well known to have been consumed by indigenous peoples since before the eighteenth century, and in many forms. Young leaves of the plant were chewed as a hunger suppressant, while leafy branches were used both in pit-cooking and as a flavorant in fish stews.

It has been found that compositions comprising an extract of the *Gaultheria shallon* or salal plant exhibit effective antimicrobial properties, especially against the bacterium *S. aureus* and the fungus Verticillium. As used herein, "antimicrobial" is intended to include bactericidal and fungicidal activity. While it is believed that virtually any part of the plant possesses the as yet unidentified antimicrobial agent, leaves, flowers and berries are preferred sources of the active agent.

The extract is formed by obtaining a portion of at least one part of the salal plant, sterilizing the same with a mild sterilizing agent such as common bleach (aqueous solution of sodium hypochlorite), rinsing the sterilizing agent from the plant, contacting the plant with an aqueous buffered solution to extract the active agent-containing portion, and drying the same at relatively modest temperatures.

Additional optional steps include reconstituting the antimicrobial agent-containing portion with sterile water and further sterilizing the same, preferably by a non-destructive sterilization process such as by microfiltration.

When the plant parts are gathered in the field, they may be simply packaged following the initial sterilization and rinsing treatments or they may be steamed to destroy enzymatic agents that might contribute to self-degradation or they may be rapidly frozen so as to preserve all potential antimicrobial agents and related compounds.

The following examples are given to demonstrate the invention only and are not to be regarded as limiting the invention in any respect.

EXAMPLES 1–4

Salal plants were located in the northwest part of the Pacific Coast. Flowers, berries and leaves of the plant were collected and washed with a 20 vol % aqueous solution of 1.05 vol % sodium hypochlorite containing 15 vol % methanol and 0.15 vol % surfactant (TWEEN 20) in order to kill any bacteria or fungus that might be on the surface of the plant parts, followed by rinsing with deionized water and air-drying.

The sterilized and rinsed plant parts were then immediately frozen or steamed or packaged "as is" without any further treatment in the field. Freezing was conducted by placing the plant part(s) in a plastic bag with approximately 75–125 cc deionized water and dipping the bag in an acetone/dry ice bath, then stored in an insulated container. Steaming was conducted so as to destroy any enzymes that might contribute to the breakdown of any biological constituents and was conducted by steaming in a pressure cooker for 20 minutes at 100°–110° C., followed by packaging the steamed plant parts in glass containers.

The frozen, steamed and "as is" samples were then taken to a laboratory for further treatment.

An aqueous buffer solution was prepared consisting of 100 mM tris-HCl and 1 mM EDTA in water, giving the solution a pH of 7.4. Plant parts along with the buffer solution were comminuted in a vortex blender and 40 mL portions of extracts were placed in 50 mL centrifuge tubes, which were then filled with the buffered solution and centrifuged at 14,000 rpm for 30 minutes. Thirty mL of the supernatant from each centrifuged sample were subjected to non-pressurized, gravity fed dialysis through a dialysis-type membrane having a molecular weight cutoff of 3500 daltons (SPECTRA/POR No. 132–76, Spectrum Chemicals). Dialyses was performed by placing the sample in a bag of the dialysis membrane, then placing the sample-containing dialysis membrane in cold (5° C.) deionized water (500 ml) for 30 hours, with changes of the dialysate water every 6 hours during the 30-hour period.

The entire solution resulting from the dialysis was transferred to a lyophilization chamber and dried under 60 milliTorr of vacuum at −40° C. overnight. The so-dried samples were then reconstituted with 5 mL of deionized water and subjected to non-destructive sterilization by microfiltration with a Millex-GV filtration unit having a membrane with 0.22 $\mu$m diameter pores (Millipore, Bedford, Massachusetts). Samples were stored in 15 mL test tubes in a freezer until tested for antimicrobial activity.

From the foregoing procedures, four extracts were assayed for bactericidal activity: flowers that had been frozen in the field (Example 1); flowers taken from the field "as is" (Example 2); flowers that had been steamed in the field (Example 3); and berries that had been frozen in the field (Example 4). For bioassays *S. aureus* was cultured in Brain Heart Infusion (BHI) media at 37° C. overnight in an orbital shaker set at 225 rpm to obtain approximately $10^5$ cells per mL of culture medium.

After culturing overnight, 100 $\mu$L aliquots, each containing a bacteria count of about $10^4$, were added to each well containing 100 $\mu$L of each of the extracts in a 96-well microplate. Control wells did not receive any bacteria. After culturing an additional 12 hours, the relative number of bacteria in each well was evaluated in triplicate by measuring optical density (turbidity) with a spectrophotometer on a microplate reader (Microplate Autoreader EL 309, Bio-Tek, Carson City, Nevada) set at a wavelength of 515 nm. The entire bioassay was repeated for a second set of samples. The average relative population of *S. aureus*, comprising the ratio of optical density for the sample to the optical density of the control culture, of the two sets of bioassays, rounded to the nearest whole percentage point, are reported in Table 1

TABLE 1

| Example No. | Plant Part | Field Processing | Dilution | Relative Population *S. aureus* |
|---|---|---|---|---|
| 1 | Flowers | Freezing | 1:90 | 2% |
|   |         |          | 1:1800 | 22% |
| 2 | Flowers | As Is | 1:90 | 31% |
|   |         |       | 1:1800 | 71% |
| 3 | Flowers | Steaming | 1:90 | 47% |
|   |         |          | 1:1800 | 62% |
| 4 | Berries | Freezing | 1:90 | 11% |
|   |         |          | 1:1800 | 65% |

EXAMPLE 5

An extract of flowers that had been frozen in the field was prepared as in Examples 1–4 and assayed twice for antibacterial activity against *S. aureus* as in Examples 1–4. Lower optical density values indicate a less dense bacteria cell population, with a value of 0.00 indicating a zero viable cell count. The average of the two measured bioassay values are reported in Table 2.

TABLE 2

| Dilution | Optical Density |
|---|---|
| 1:90 | 0.00 |
| 1:900 | 0.00 |
| 1:1500 | 0.09 |
| 1:3000 | 0.35 |
| 1:6000 | 0.35 |

EXAMPLES 6–7

Extracts of flowers (Example 6) and leaves (Example 7) that had been left "as is" in the field were prepared as in Examples 1–4 and were assayed for fungicidal activity against Verticillium by culturing the extracts with the Verticillium spore condidium in Czapek's agar media for 3 days and for 7 days for colony growth. One plate for each of the two extracts was inoculated with 0.02 mL of a suspension of the conidia spore and adjusted to approximately $10^4$ colony-forming units/mL. Plates were examined under the microscope to determine conidium germination. Colony growth was determined by examination of the colony diameter and rated as: += some inhibition (less than one-half the control diameter); ++= moderate inhibition (less than one-fourth the control diameter); and +++= complete inhibition (no visible growth). A plate containing Czapek's agar alone was used as a positive control so as to permit uninhibited growth. Czapek's agar with the antibiotic pimaricin added was used as a negative control so as to completely inhibit growth. The assay results are summarized in Table 3.

TABLE 3

| Example No. | Dilution | Antifungal Activity |
|---|---|---|
| 6 | 1:100 | ++ |
|   | 1:1000 | + |
| 7 | 1:100 | +++ |
|   | 1:1000 | ++ |

The terms and expressions which have been employed in the foregoing specification are used therein as terms of description and not of limitation, and there is no intention in the use of such terms and expressions of excluding equivalents of the features shown and described or portions thereof, it being recognized that the scope of the invention is defined and limited only by the claims which follow.

What is claimed is:

1. An antimicrobial composition comprising an effective amount of an antimicrobial agent comprising an extract of the plant *Gaultheria shallon*.

2. The composition of claim 1 wherein said antimicrobial agent is bactericidal.

3. The composition of claim 1 wherein said antimicrobial agent is fungicidal.

4. The composition of any of claims 1–3 wherein said extract is of a part of said plant selected from the group consisting of flowers, berries, leaves and mixtures thereof.

5. The composition of claim 4 wherein said extract is of flowers of said plant.

6. The composition of claim 4 wherein said extract is of berries of said plant.

7. The composition of claim 4 wherein said extract is of leaves of said plant.

8. The composition of any of claims 1–3 wherein said extract is an aqueous-based extract.

9. The composition of claim 8 wherein said extract is obtained by contact with an aqueous buffered solution.

10. A method of obtaining an antimicrobial agent comprising the following steps:
   (a) obtaining a portion of at least one plant part of the plant *Gaultheria shallon;*
   (b) sterilizing said plant portion;
   (c) rinsing said plant portion;
   (d) contacting said plant portion with an aqueous buffered solution to obtain a supernatant;
   (e) separating an antimicrobial agent-containing portion from said supernatant by filtration; and
   (f) drying said antimicrobial agent-containing portion.

11. The method of claim 10 wherein step (b) is conducted by contacting said plant portion with a hypochlorite solution.

12. The method of claim 10 wherein, following step (c), said plant portion is processed by a method selected from freezing and steaming.

13. The method of claim 12 wherein said freezing is conducted rapidly.

14. The method of claim 10 wherein said aqueous buffered solution of step (d) comprises tris-HCl and EDTA at pH 7.4.

15. The method of claim 10 wherein step (e) is conducted by dialysis.

16. The method of claim 15 wherein said dialysis membrane has a molecular weight cut-off of 3500 daltons.

17. The method of claim 10 wherein step (f) is conducted by vacuum drying.

18. The method of claim 10, including an additional step (g) of reconstituting said antimicrobial agent-containing portion with sterile water.

19. The method of claim 18, including an additional step (h) of further sterilizing said antimicrobial agent-containing portion.

20. The method of claim 19 wherein step (h) is conducted by microfiltration.

21. The product of the method of any of claims 10–13 or 15–17.

* * * * *

UNITED STATES PATENT AND TRADEMARK OFFICE
CERTIFICATE OF CORRECTION

PATENT NO. : 6,268,399 B1
DATED : July 31, 2001
INVENTOR(S) : Hultine et al.

It is certified that error appears in the above-identified patent and that said Letters Patent is hereby corrected as shown below:

Column 4,
Line 20, change "condidium" to read -- conidium --

Signed and Sealed this

Twenty-sixth Day of February, 2002

Attest:

Attesting Officer

JAMES E. ROGAN
Director of the United States Patent and Trademark Office